United States Patent
Sigrist et al.

(10) Patent No.: US 6,346,376 B1
(45) Date of Patent: Feb. 12, 2002

(54) OPTICAL SENSOR UNIT AND PROCEDURE FOR THE ULTRASENSITIVE DETECTION OF CHEMICAL OR BIOCHEMICAL ANALYTES

(75) Inventors: Hans Sigrist, Kernenried; Hui Gao, Neuchâtel; Rino E. Kunz, Steinmaur; Jürg Dübendorfer, Zurich; Carsten Korth, Zurich; Markus Moser, Zurich; Bruno Oesch, Stilli, all of (CH)

(73) Assignee: Centre Suisse d'Electronique et de Mictotechnique SA (CH)

( * ) Notice: Subject to any disclaimer, the term of this patent is extended or adjusted under 35 U.S.C. 154(b) by 0 days.

(21) Appl. No.: 09/309,546

(22) Filed: May 11, 1999

(30) Foreign Application Priority Data

Jun. 9, 1998 (EP) .............................. 98810508

(51) Int. Cl.⁷ ........................................... G01N 33/543
(52) U.S. Cl. ...................... 435/5; 356/128; 356/130; 422/68.1; 422/81; 422/99; 435/4; 435/6; 435/7.1; 435/287.1; 435/287.2; 435/288.7; 435/800; 436/501; 436/518; 436/524; 436/527; 436/528; 436/535; 436/805
(58) Field of Search .................. 435/4, 287.2, 7.1, 435/287.1, 288.7, 808, 6; 436/501, 518, 524, 527, 528, 535, 805; 422/68.1, 81, 99; 356/128, 130

(56) References Cited

U.S. PATENT DOCUMENTS

| | | | |
|---|---|---|---|
| 4,204,037 A | | 5/1980 | Dill et al. .................. 435/3 |
| 4,521,522 A | * | 6/1985 | Lundstrom et al. ......... 436/525 |
| 4,558,012 A | * | 12/1985 | Nygren et al. ............. 436/501 |
| 5,017,009 A | * | 5/1991 | Schutt et al. ............. 358/338 |
| 5,071,248 A | * | 12/1991 | Tiefenthaler et al. ....... 356/128 |
| 5,225,374 A | * | 7/1993 | Fare et al. ................ 437/225 |
| 5,313,264 A | * | 5/1994 | Ivarsson et al. ............ 356/73 |
| 5,327,225 A | * | 7/1994 | Bender et al. ............. 356/445 |
| 5,455,178 A | * | 10/1995 | Fattinger ................. 436/164 |
| 5,485,277 A | * | 1/1996 | Foster .................... 456/445 |

(List continued on next page.)

FOREIGN PATENT DOCUMENTS

| | | | |
|---|---|---|---|
| WO | WO 89/10551 | 11/1989 | |
| WO | WO 96/35940 | * 11/1996 | .......... G01N/21/77 |
| WO | WO 97/12225 | 4/1997 | |

OTHER PUBLICATIONS

Bockman et al. (1988). Immunological analysis of host and agent effects on Creutzfeldt–Jacob disease and scrapie prion proteins. J. Virol. 62(9):3120–3127.*

Gale et al. (1995). Polymer and III–V transducer platferms for integrated optical sensors. Optical Eng. 34(8):2396–2406.*

(List continued on next page.)

Primary Examiner—Christopher L. Chin
(74) Attorney, Agent, or Firm—Parkhurst & Wendel, L.L.P

(57) ABSTRACT

This document describes an optical sensor unit and a procedure for the specific detection and identification of biomolecules at high sensitivity in real fluids and tissue homogenates. High detection limits are reached by the combination of i) label-free integrated optical detection of molecular interactions, ii) the use of specific bioconstituents for sensitive detection and iii) planar optical transducer surfaces appropriately engineered for suppression of non-specific binding, internal referencing and calibration. Applications include the detection of prion proteins and identification of those biomolecules which non-covalently interact with surface immobilized prion proteins and are intrinsically involved in the cause of prion related disease.

15 Claims, 5 Drawing Sheets

U.S. PATENT DOCUMENTS

| | | | | |
|---|---|---|---|---|
| 5,573,956 A | * | 11/1996 | Hanning | 436/518 |
| 5,622,872 A | * | 4/1997 | Ribi | 436/518 |
| 5,623,561 A | * | 4/1997 | Hartman | 385/12 |
| 5,633,724 A | * | 5/1997 | King et al. | 356/445 |
| 5,641,640 A | * | 6/1997 | Hanning | 435/739.2 |
| 5,843,651 A | * | 12/1998 | Stimpson et al. | 435/6 |
| 5,919,712 A | * | 7/1999 | Herron et al. | 436/518 |
| 5,961,924 A | * | 10/1999 | Reichert et al. | 422/82.11 |
| 5,986,066 A | * | 11/1999 | Barner et al. | 530/391.1 |
| 6,008,435 A | * | 12/1999 | Prusiner et al. | 800/18 |

OTHER PUBLICATIONS

"Polymer and III–V Transducer Platforms for Integrated Optical Sensors"; M.T. Gale; vol. 34, No. 8; Aug. 1995; pp. 2396–2406; XP000518235; Bellingham, WA; * p. 2396, left–hand col., para. 1* *p. 2396, right–hand col., line 13–p. 2397, left–hand col., line 7* *p. 2397, right–hand col., lines 22–37* *p. 2400, right–hand col., para. 2* *p. 2402, left–hand col., lines 1–12 and 28–41* *p. 2404, left–hand col., lines 11–20* *p. 2404, right–hand col., last para.–p.2405, left–hand col., line 8; figures 1, 3A, 8, 11*.

* cited by examiner

OPTICAL SENSOR UNIT AND PROCEDURE FOR THE ULTRASENSITIVE DETECTION OF CHEMICAL OR BIOCHEMICAL ANALYTES

FIELD OF THE INVENTION

The present invention relates to an optical sensor unit and to a procedure for accurate and ultrasensitive detection of chemical or biochemical analytes. An optical sensor unit is described combining several unique parts inching a laser light source, an optical detection module, and an integrated optical transducer chip. The optical transducer chip consists of a disposable carrier substrate coated with a waveguiding layer onto which sensing biomolecules are bonded in pattern fashion, said sensing biomolecules being capable of interacting with chemicals or bio-molecules of an analyte solution to induce changes in the effective refractive index.

More particularly, the invention relates to the detection of prions and prion binding molecules in pico- to femto-molar concentrations with the help of antibodies, preferably monoclonal, allowing specific detection of disease-specific prion proteins on surfaces engineered for low non specific binding of bioconstituents. Conversely, the biosensor is applicable to identify ligands to prion proteins if instead of the monoclonal antibodies, recombinant or highly purified PrP is bonded to the optical chip by a one-step procedure, which can be performed even by those not skilled in the art.

More generally, the sensor and the procedure according to the invention facilitates ligand screening of chemical and biochemical libraries.

BACKGROUND OF THE INVENTION

As the detection of prions and prion binding molecules is at this time of upmost importance for diagnosing and treating prion related diseases, this aspect will serve as guideline for the description of the invention. For a better understanding the abbreviations used hereinbefore and hereinafter are the following:

| | |
|---|---|
| BSA | bovine serum albumin |
| BSE | bovine spongiform encephalopathy |
| CJD | Creutzfeldt-Jakob disease |
| EDTA | ethylenediaminetetraacetic acid |
| GPI-anchor | glycolipid-anchor which "ties" PrP to the outer monolayer of the cell membrane |
| HEPES | hydroxyethyl-piperazineethane sulfonic acid |
| IO | integrated optical |
| PBS | phosphate-buffered saline |
| prion | proteinaceous infectious particle; the infectious agent of prion diseases, supposedly consisting at least of $PrP^{sc}$ and maybe another (other) yet unknown molecule(s) |
| PrP | prion protein; refers to the common amino acid sequence rather than to a distinct conformation of two prion protein isoforms |
| $PrP^c$ | a normal host prion protein of unknown function; apparent molecular weight 33–35 kDa, same amino acid chain, and same glycosylation at two asparagine residues as $PrP^{Sc}$. This prion protein is after proteinase K treatment fully digested. |
| $PrP^{Sc}$ | the disease-specific, abnormal isoform of $PrP^c$, with the same amino acid chain, apparent molecular weight 33–35 kDa, glycosylated at two asparagine residues, is after proteinase K treatment shortened to a 27–30 kDa C-terminal fragment. Species-specific $PrP^{Sc}$ isoforms may term: human $PrP^{Sc}$ (instead of $PrP^{CID}$), bovine $PrP^{Sc}$ (instead of $PrP^{BSE}$) etc. |

-continued

| | |
|---|---|
| rb PrP | recombinant bovine prion protein (amino acids 25 to 242 of the bovine PrP gene) expressed in *E. coli* comprising the bovine PrP open reading frame except for the N-terminal signal sequence and the C-terminal GPI-anchor sequence; both are cleaved off during cellular processing. Since this protein is not glycosylated it has a molecular weight of 23 kD. |
| SPOT | smart planar optical transducer |

The references to the prior art reported hereinafter will be termed by the name of the first author and the publication year as mentioned below:

Basler, K., Oesch, B., Scott, M., Westaway, D., Walchli, M., Groth, D. F., Mc Kinley, M. P, Prusiner, S. B., and Weissmann, C. (1986). Scrapie and cellular PrP isoforms are encoded by the same chromosomal gene. Cell 46, 417–428.

Borchelt, D. R., Scott, M., Taraboulos, A., Stahl, N., and Prusiner, S. B. (1990). Scrapie and cellular prion proteins differ in their kinetics of synthesis and topology in cultured cells. J. Cell Biol. 110, 743–752.

Bueler, H., Fischer, M., Lang, Y., Bluethmann, H., Lipp, H. P., DeArmond, S. J., Prusiner, S. B., Aguet, M., and Weissmann, C. (1992). Normal development and behaviour of mice lacking the neuronal cellsurface PrP protein. Nature 356, 577–582.

Düibendorfer, J., Kunz, R. E., Mader, E., Duveneck, G. L. and Ehrat, M. (1996) "Reference and Sensing Pads for Integrated optical Immunosensors," Proc. SPIE, Vol. 2928, 90–97.

Gao, H., Kisling, E., Oranth, N., and Sigrist, H. (1994). Photolinker-polymer-mediated immobilization of monoclonal antibodies, $F(ab')_2$ and F(ab') fragments. Biotechnol. Appl. Biochem. 20, 251–263.

Gao, H., Sänger, M., Luginbüihl, R., Sigrist, H., Immunosensing with photo-immobilized immunoreagents on planar optical wave guides. Biosensors & Bioelectronics 10 (1995) 317–328.

Heding, A., Gill, R., Ogawa, Y., De Meyts, P, Shymko, R. M. (1996). Biosensor measurement of the binding of insulin-like growth factors I and II and their analogues to the insulin-like growth factorbinding protein-3. J. Biol. Chem. 271, 13948–52.

Kitamoto, T., Mohri, S., and Tateishi, J. (1989). Organ distribution of proteinase-resistant prion protein in humans and mice with Creutzfeldt-Jakob disease. J. Gen. Virol. 70, 3371–3379.

Korth, C., Stierli, B., Moser, M., Streit, P., Oesch, B. (1997) Immunological detection of prions. European Patent application No. 97102837.8.

Kunz R. E., "Process and device for determining quantities to be measured by means of an integrated optical sensor module", U.S. Pat. No 5,442,169.

Kunz R. E., "Integrated Optical Sensors based on Hard Dielectric Films on Replicated Plastic Substrates", Proc. 8th Eur. Conf. Integrated optics ECIO,97, Stockholm, Sweden, April 2–4, 1997, pp. 86–93.

Kunz, R. E. (1996). "Integrated Optical Modules for Chemical and Biochemical Sensing". Bulletin of the Swiss Microtechniques Association (ASMT) 20,48–53.

Kunz, R. E, and Dübendorfer, J. (1995). "Miniature Integrated Optical Wavelength Analyzer Chip". Optics Letters 20, 2300–2303.

Kunz, R. E., and Dübendorfer, J. (1996). "Novel Miniature Integrated Optical Goniometers". Proc. EUROSENSORS X, Conference on Solid-State Transducers 3,905–908.

Kunz, R. E., Duveneck, G., and Ehrat, M., (1994). "Sensing Pads for Hybrid and Monolithic Integrated Optical Immunosensors", Proc. SPIE 2331, 2–17.

Kunz, R. E., Edlinger, J., Sixt, P., and Gale, M. T. (1995) Replicated Chirped Waveguide Gratings for Optical Sensing Applications. Sensors and Actuators 47, 482–486.

Kurschner, C. and Morgan, J. I. (1995). "The cellular prion protein (PrP) selectively binds to bcl-2 in the yeast two-hybrid system. Molecular. Brain Research. 30, 165–168.

Lukosz, W. and Tiefenthaler, K., "Directional switching in planar waveguides effected by absorption-desorption processes," IEE Conf. Publ. 227, 152–155 (1983).

Oesch, B. (1994). "Characterization of PrP binding proteins". Philos. Trans. R. Soc. Lond. B. Biol. Sci. 343, 443–445.

Oesch, B., Westaway, D., Walchli, M., McKinley, M. P., Kent, S. B., Aebersold, R., Barry, R. A., Tempst, P., Teplow, D. B., and Hood, L. E. (1985). "A cellular gene encodes scrapie PrP 27–30 protein". Cell 40, 735–746.

Oesch, B., Teplow, D. B., Stahl, N., Serban, D., Hood, L. E., and Prusiner, S. B. (1990). "Identification of cellular proteins binding to the scrapie prion protein". Biochemistry 29, 5848–5855.

Serban, D., Taraboulos, A., DeArmond, S. J., and Prusiner, S. B. (1990). "Rapid detection of Creutzfeldt-Jakob disease and scrapie prion proteins". Neurology 40, 110–117.

Stahl, N., Baldwin, M. A., Teplow, D. B., Hood, L., Gibson, B. W., Burlingame, A. L., and Prusiner, S. B. (1993). "Structural studies of the scrapie prion protein using mass spectrometry and amino acid sequencing". Biochemistry 32, 1991–2002.

The disease-specific forms of the prion protein ($PrP^{Sc}$, $PrP^{BSE}$) are part of the infectious particle causing transmissible neurodegenerative diseases like scrapie in sheep, bovine spongiform encephalopathy in cattle or Creutzfeldt-Jakob disease in humans. $PrP^{Sc}$ as well as $PrP^{BSE}$ differ from the normal cellular prion protein ($PrP^c$) by their relative protease resistance (Oesch, 1985). The molecular changes leading to this difference in physicochemical properties are unknown. Protease-resistant $PrP^{Sc}$ and infectivity to date have not been separated, leading to the proposal that the infectious particle would be composed of specifically altered PrP molecules. The primary amino acid sequence of $PrP^{Sc}$ is identical to that predicted from its cDNA sequence or genomic nucleic acid sequence (Stahl, 1993) and the infectious particle does not encode an altered PrP gene (Oesch, 1985). In cell culture, $PrP^c$ is converted into $PrP^{Sc}$ posttranslationally (Borchelt, 1990). However, no differences in covalent modifications of $PrP^{Sc}$ and $PrP^c$ were observed by mass spectrometry (Stahl, 1993). The lack of a molecular explanation for the observed differences between $PrP^{Sc}$ and $PrP^c$ led to the proposal that the PrP isoforms differ in their conformation (Basler,1986). The relative protease resistance of $PrP^{Sc}$, e.g. $PrP^c$ being fragmented by proteinase K and $PrP^{Sc}$ being partially resistant to the action of proteinase K, is at this time the usual way to distinguish the two forms of PrP (Serban, 1990).

$PrP^{Sc}$ is currently detected by Western or dot blotting. After protease digestion, the molecular weight of $PrP^{Sc}$ is reduced from 33–35 kDa to 27–30 kDa (PrP 27–30). This characteristic change in molecular weight is detected by Western blotting and serves as a hallmark of $PrP^{Sc}$. As an alternative, PrP 27–30 can be detected on dot blots (Oesch, 1994; Korth, 1997). Native PrP 27–30 is not recognized by antibodies, whereas the denatured form of the protein interacts with antibodies. (Serban, 1990). Circumstantial evidence indicates that the epitopes in $PrP^c$ and $PrP^{Sc}$ differ in accessibility. Previously, it has been attempted without success to generate antibodies which specifically recognize $PrP^{Sc}$, thus limiting the immunological detection methods to procedures including denaturation of samples prior to detection. However, (Korth, 1997) described monoclonal antibodies (see below) that do allow detection of native $PrP^{Sc}$ and, specifically, $PrP^{BSE}$.

A receptor for PrP transducing biological effects of PrP has not been found yet. Until now, various proteins have been shown to interact with PrP: glial fibrillary acidic protein (GFAP); (Oesch, 1990), bcl-2 (Kurschner, 1995). All of these proteins are intracellular proteins which contrasts with the cell surface location of PrP. Even though there may be a role for these PrP binding proteins, in particular bcl-2, in the neurotoxic effects of $PrP^{Sc}$ it is postulated that a cell surface protein should exist which binds to PrP. Despite the scientific investigations summarized above, there is still a need for a detection system which impairs as little as possible the conformation of the molecules or biomolecules to be detected.

Indeed, known analyte detection techniques have their limitations in terms of sensitivity and quantification, the procedure involving several steps, the necessity of detection of labelled components and the overall duration of the test procedure.

With the present invention, these shortcomings are overcome by the use of biosensors which allow the registration of molecular interactions at the surface of integrated optical chips. The basic principle of these biosensors is to measure the change in the effective refractive index for the guided waves on an optical chip when a ligand interacts non-covalently with molecules bonded to the surface of the respective chip. The specificity of the interaction is ascertained by the use of molecules such as antibodies immobilized on the surface of integrated optical chips. The described $PrP^{BSE}$ biosensor detection system is based on an optical transducer in combination with miniature integrated optical sensor devices. Optical waveguide sensing provides the features of exceptional high sensitivity and label free detection of analytes within the evanescent field of incoupled laser light. Requirements for high selectivity, reduction of non-specific binding and multiple sensing on a single waveguide surface are accomplished by appropriate sensor surface bioengineering combined with multidomain photobonding. The use of multidomain analysis on integrated optical chips dramatically simplifies the instrumental features of the detection system. Multidomain analysis on a single chip enables integrated calibration and referencing. The described prion detection system in combination with unique monoclonal antibodies is used to detect $PRP^{BSE}$ with high sensitivity and high speed. It allows to screen large numbers of samples.

With the same detection system, on the other hand, biomolecules interacting with PrP can be identified. For this purpose, instead of covalently bonding monoclonal antibodies to PrP, rb PRP or highly purified native PrP, $PrP^c$ or $PrP^{Sc}$ is immobilized on the surface of the optical chip. Since. applied detection principles do not require labelling of a probe, it is exquisitely suited to search for (an) elusive "PrP receptor(s)" which is (are) currently unknown but postulated to be essentially involved in the modulation of PrP function as well as in the infection of cells by prions.

The described biosensor system further suits the screening of chemical libraries in search for potential ligands which interact with molecules bonded to optical chips. For example, PrP bonded on an optical chip allows one to screen for chemical ligands capable of preventing neurotoxic and infectious properties of prions.

OBJECT OF THE INVENTION

It is the object of the present invention to overcome the drawbacks and failures of prior art like complex multistep procedures, limited sensitivity, necessity of label-based analyte detection and necessity of sophisticated equipment. These limitations are addressed in the present invention, which provides an accurate and ultrasensitive detection system for biological ligands, especially prion proteins and proteins which interact with prion proteins, to be used in the diagnosis of prion diseases, or any other biological state involving detection of molecules in biological fluids or tissue homogenates and requiring high sensitivity.

SUMMARY OF THE INVENTION

The present invention describes a novel sensor system which is able to detect and quantify pico- to femto-molar concentrations of chemicals or bio- molecules in analytes of biological origin in real fluids. Analytical limitations of hitherto systems are overcome by combining the exceptional sensitivity of a new design for simplified integrated optical detection on disposable sensor chips with the intrinsic specificity of sensing bioconstituents and photobonding and biopatten technologies enabling both array detection and integrated calibration. Teachings include the design of the biosensor system and its essential components, the design and fabrication of multi-array biosensor chips and the preparation and characteristics of high-affinity disease-specific bioconstituents. General use of the biosensor system for on-site application is exemplified with the detection of $PrP^{BSE}$ in homogenates of brain and the detection of molecular components participating in prion related diseases, e.g. identification of $PrP^{BSE}$ binding biomolecules.

The present invention concerns the layout and description of the modular system components of the analytical instrument. In its final form, the instrument is portable and at least consists of a laser light source, an optical detection module and an integrated optical transducer chip. This instrument can be extended with an effector system, such as a fluid handling system for allowing the selection of individual samples, solvents or washing solutions, and with an appropriate computer-like component for data storage, processing and presentation.

The surface of the integrated optical transducer chip can be grafted with lipids, forming lipid bilayer surfaces, serving as a membrane mimetic systems for the integration of membrane receptor proteins.

Sensor pad illumination is achieved by directing the radiation from sources such as laser diodes in the red or near infra-red wavelength region (e.g. Sharp LT026MDO, $\lambda$~785 nm), either directly or via optical fibers. The optical output signal is detected by one- or two-dimensional detector devices, such as charge coupled devices (CCDs), photodiode arrays (PDAs), such as Hamamatsu S5463, or position sensitive devices (PSDs). The signal is evaluated and stored in digitized form and prepared for transmission to the computer component, e.g. RS232 interface.

In a preferred embodiment, the optical transducer chip consists of a high refractive index dielectric waveguiding film (e.g. $TiO_2$, $Si_3N_4$, mixtures of $TiO_2$ and $Si_3N_4$, $Ta_2O_5$, $ZrO_2$, $HfO_2$, $Nb_2O_5$), coated on a previously structured substrate (e.g. polycarbonate or polystyrene). The substrate is structured with (chirped) grating pads by means of procedures, as e.g. hot-embossing or injection moulding. The grating pads fulfill the tasks of coupling the light into the waveguiding film, of on-chip signal generation and of coupling the light out of the waveguide and directing it to the detector. A typical size of one sensor pad is in the order of a few $mm^2$. Arrays of sensor pads can be accomplished by placing several pads next to each other. Using sensor pad arrays is advantageous for chemical multicomponent analysis and on-chip referencing. Preferred shapes of the biosensor chip are rectangular (card) or circular (disc). If the transducer is in the form of a disc, the disc is rotated on a central axis and contains optical on-chip elements for speed control and pad-specific information (e.g. position, sensing layer etc.). In the disc format, the sensing pads are arranged in concentric circles or in spiral arrangements. Either each pad is addressed consecutively, or several, or all pads can be interrogated in parallel by means of single or multiple beam illumination, e.g. by means of light source and detector arrays.

The sample holder consists either of an open cell allowing manual sample application, or it consists of a closed cell with tubings (e.g. Teflon, Peek) and a suitable liquid handling system.

The present invention concerns further a process for chip surface engineering including bonding of biomolecules, such as PrP, monoclonal or polyclonal antibodies, mixtures of monoclonal antibodies or other proteins which recognize specific epitopes on the target proteins (e.g. PrP). In a preferred embodiment, these proteins or antibodies are covalently immobilized on the waveguiding surfaces by means of photolinker polymer mediated photobonding or by oriented immobilization of analyte recognizing receptor molecules, genetically engineered receptor molecules or fragments of analyte recognizing immunoreagents through surface grafting with e.g. bifunctional photoactivatable maleimides. As an alternative, antibodies or other proteins are immobilized on the chip surface by absorption.

In addition to the immobilization methods discussed above, the layer of sensing bimolecules can be immobilized on the surface of a wave guiding layer by Langmuir-Blodgett techniques.

The present invention concerns further the process of engineering of the optical transducer surface with sensing biomolecules appropriate for analyte detection. Using mask-free or mask-assisted patterning procedures, the individual pads on the optical transducer surface are individually functionalized with selected molecules and varying compositions of biomolecules. For referencing, given sets of pads are modified with non-specific interacting analogs of the specific analyte-binding molecules, and on chip referencing is attained by sets of pads which provide increasing amounts of specific analyte binding molecules. Differential analyte binding kinetic data recorded from these calibration pads allow on-chip analyte calibration with reference to established binding constants.

The present invention concerns further a process, in which non-specific binding of bioconstituents present in the analyte fluid is suppressed by surface coating with polyethylene glycol, antibodies which do not interact with the ligand, polycarbohydrates, carbohydrates presenting low molecular weight photolinkers, or mixtures of the components mentioned.

The invention concerns further a procedure for verifying the proper functioning of the integrated optical transducer in situ, before and after each measurement by varying the incidence and/or the wavelength of the light.

The present invention concerns further a process in which the output signal light of a first optical sensor unit can be used to regulate, optionally by means of a computer, a second effector system and thus allowing the automation of biochemical reactions involving many single sequential or parallel steps.

The present invention concerns further a combination of the analytical detection system, the optical biosensor module bonded with monoclonal antibodies to PrP able to detect PrP in a fluid guided to the optical sensor unit.

The present invention concerns further a combination of the analytical detection system, the optical biosensor module with photobonded or oriented immobilized PrP able to detect biomolecules which non-covalently interact with said immobilized PrP.

The present invention concerns further a process for the identification and medical use of those biomolecules which can be detected and identified after non-covalent binding to surface-bonded PrP if said biomolecules inhibit the propagation of PrP destabilization or reverse PrP unfolding.

DETAILED DESCRIPTION OF THE INVENTION

Figure 1A:
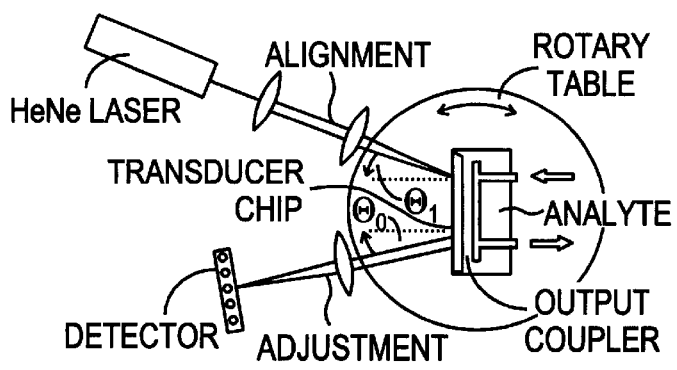
FIG. 1 is a schematic representation of two IO sensor system types: (a) conventional arrangement (type I) and (b) novel compact miniature detection unit (type II)
Figure 1B:
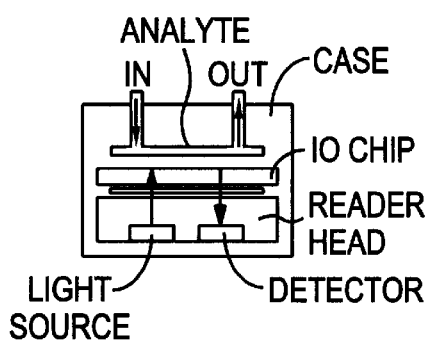

In the following detailed description the spirit and scope of the invention will become more clearly explained.
The Monoclonal Antibodies A monoclonal antibody according to the invention is defined as a biomolecule which binds to epitopes of prion proteins, whether they are in soluble or insoluble form in various tissue specimens, such as homogenates or sections of brain, spleen, tonsils, white blood cells, or others, and body fluids, such as blood, cerebrospinal fluid, saliva, urine, or others. The present mABs bind to epitopes of amino acids in a row or to epitopes of amino acids on different loops of the three-dimensional structure of native PrPs, which are spatially close to each other. A particular group of the present antibodies binds only to native disease-specific PrP and not to native normal PrP. Particular antibodies, termed 6H4, 34C9, 15B3 according to the invention, are more detailed in (Korth, 1997).

The term monoclonal antibody comprises also chimeric monoclonal antibodies having similar properties, which are derived from different animals, such as human/mouse chimeric antibodies or any other chimeric molecule comprising the antigen-binding part of the monoclonal antibody (idiotype) with other molecules such as antibody fragments of other monoclonal antibodies or enzymes.

A fragment of a monoclonal antibody comprising the binding part of the monoclonal antibody (idiotype) is likewise capable of specifically binding the antigen and is termed F(ab) or F(ab')$_2$, depending on whether the monoclonal antibody is digested with papain or pepsin, respectively.

A synthetic antibody or fragments thereof is designed according to the amino acids or substituted homologous amino acids composing the idiotype responsible for binding the antigen. Homologous amino acids are defined as exchanges within the following five groups: 1. Small aliphatic, nonpolar or slightly polar residues: alanine, serine, threonine, glycine, proline; 2. Polar, negatively charged residues and their amides: aspartic acid, asparagine, glutamic acid, glutamine; 3. Polar, positively charged residues: histidine, arginine, lysine; 4. Large aliphatic, nonpolar residues: methionine, leucine, isoleucine, valine, cysteine; 5. Large aromatic residues: phenylalanine, tyrosine, tryptophan.

The antibodies and fragments thereof are essential tools for immunological detection procedures based on the binding of the prion protein to the presented monoclonal antibodies in an antigen-antibody complex. The monoclonal antibodies of the invention react with recombinant bovine PrP as well as native or denatured PrP$^c$ and PrP$^{Sc}$, whether they are in soluble or insoluble state. The monoclonal antibodies react furtheron with PrP from different species, for example humans, hamsters, pigs, sheep, cattle and mice.
Anti-idiotype Antibodies The invention concerns further anti-idiotype antibodies which are antibodies that bind with the binding region (idiotype) to the binding region of the original monoclonal antibody. The anti-idiotype antibody mimicks features of the original antigen, in this case features of PrP. Anti-idiotype antibodies are raised as polyclonal antibodies (serum) or monoclonal antibodies from animals immunized with the preferred antibodies according to the invention. Anti-idiotype antibodies are valuable tools in detecting and blocking interactions of the original antigen (PrP), particularly interactions with receptors, and can therefore be used in prevention and therapy of prion diseases.
The Recombinant Bovine Prion Protein The present fragment of the prion protein PrP$^c$ was purified to a homogeneity of>98% and is described in detail in (Korth, 1997). It can exist either in oxidized or reduced form. In the oxidized form, there is a single —S—S-bridge whereas, in the reduced form, two SH groups are present instead. The oxidized form has a molecular weight of 23676.8 kD, and the reduced form 236886.1 kD, as determined by mass spectroscopy.

A native prion protein PrP is the prion protein in a fully folded state, i.e. the three-dimensional structure is present. Only in the native, i.e. folded state, PrP isoforms are different (normal native vs. disease-specific native PrP).

A denatured prion protein is the prion protein in the unfolded state. This is usually achieved by the addition of chaotropic substances, such as urea or guanidinium hydrochloride. In the denatured state, both PrP isoforms are irreversibly the same, even if they have been normal native or disease-specific native before.

An antigen-antibody complex is a physical attachment of an antibody, or fragment thereof, with the corresponding antigen by intermolecular forces because the surfaces match in a unique way. The matching surface on the antibody is called idiotype and the surface on the antigen is called epitope.

The Biosensor Chip and Module

A miniature biosensor chip provides a versatile platform for biomolecule binding, quantitative detection of biomolecules and for selective retention of biomolecules. The disposable biosensor transducer chip (FIG. 4) consists of a high refractive index dielectric waveguiding film (F) deposited on a previously structured substrate (S). The substrate is structured with grating pads (G1, G2) by microstructuring technologies including hot embossing or injection moulding. The grating effects appropriate incoupling of light, signal generation and outcoupling of the light. The size of the sensor pads may vary from tens of mm$^2$ to submillimeter dimensions. The pads are arranged pairwise or serial, allowing individual and group referencing, respectively. The array sensor platform is essential for multicomponent analysis and on-chip referencing. Preferred shapes of the biosensor chip are rectangular (FIG. 4.$d$) or circular disc-shaped (FIG. 4.$e$) forms. Multi-arrays on rectangular platforms can be addressed by fibre guided light, originating from a single source or from multiple light sources. Disc-shaped optical platforms use CD technologies to address individual pads, enabling high repetitive reading frequencies and thus, fast kinetic measurements.

Figure 5:
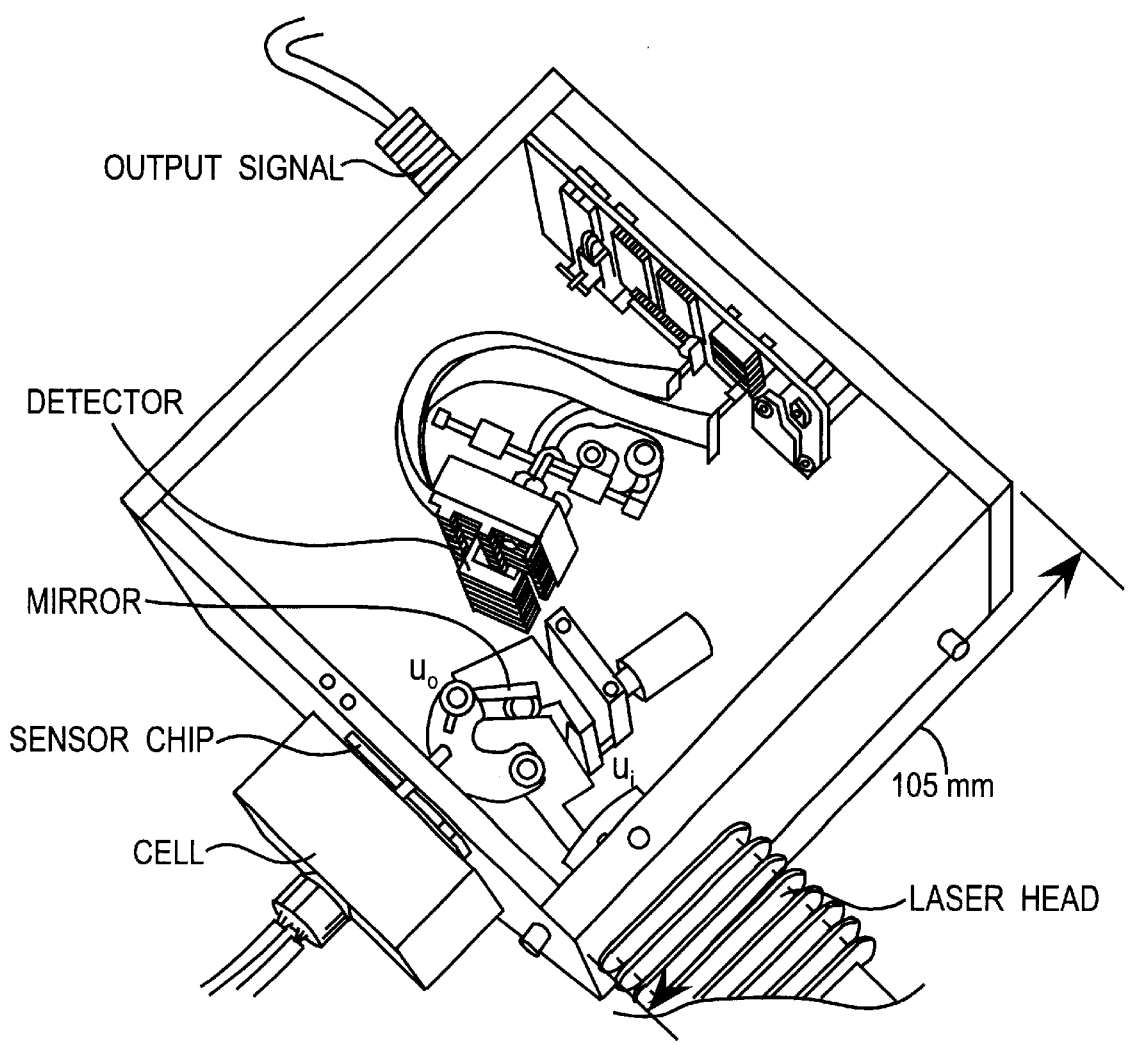
FIG. 5 shows a compact sensor module prototype based on a replicated SPOT chip.

Essential modular components of the instrument include the chip holder (FIG. 5), a fluid handling system which provides controlled analyte and buffer throughput. The fluid handling system is designed for high analyte surface interaction and minimal system surface exposure. Guided light from laser light source (Laser Head) impinges on the grated structures (Sensor Chip) and generated output signals are recorded by photodiode arrays (Detector).

Bonding of Biomolecules to the Optical Transducer Surface

Biomolecules are known to interact with material surfaces in accordance with the physico-chemical properties of the material and the biomolecule surface. Appropriate surface engineering is introduced in order to control the physical processes, enhance uniform biomolecule surface interactions and promote, optionally, covalent biomolecule binding. Covalent biomolecule binding is advantageous since it provides the means for extensive washing and thus reduction of non-specific binding of system constituents. Non-specific binding can be suppressed or prevented by introducing agents on the transducer surface which repel biomolecules. Polyethylene glycol (PEG), carbohydrates, the polar head groups of lipid bilayers, as well as selected protein layers may serve to suppress non-specific binding. Preferred processes for biomolecule binding are those which are technically easy to perform, lead to covalent binding and can be utilized for multicomponent binding. Photobonding is one of the processes which per se, or in combination with micro-dispensing methods, allows addressable printing of biomolecules on individual sensing pads. Photobonding technologies enable experimentally easy formation of pad to pad gradients providing different biomolecule densities at individual sensor pad surfaces. A preferred method of photobonding is the photopolymer mediated immobilization of biomolecules with light. The process includes mixing of the biomolecule(s) to be immobilized with a photoactivatable polymer prior to the deposition on the transducer surface. Upon exposure to light, covalent bonds are formed between the photopolymer, the biomolecules and the surface effecting photoimmobilization. A comparable process leads to the covalent bonding of a low molecular weight crosslinker to the transducer surface. If photoactivatable heterobifunctional crosslinkers are immobilized on the surface, the prerequisites are established for oriented macromolecule binding. For example, photobonding of an aryldiazirino-maleimide crosslinker provides a grafted surface to which biomolecules with reactive thiol function covalently attach. As an alternative to covalent binding of biomolecules to the chip surface, they are passively absorbed to the chip surface. Preferred conditions are concentrations of 0.5 $\mu$g /mm$^2$.

Detection Procedure of Prion Disease with Biosensors

An immunological detection procedure for prion disease, especially BSE in cattle and scrapie in sheep, whereby disease-specific PrP$^{Sc}$ protein in biological material of an animal or human comprises treatment of a first probe of said material with a monoclonal antibody to PrP and detecting the mixed $PrP^c/PrP^{Sc}$-antibody complex, treating a second probe of said material first with proteinase K and then with the monoclonal antibody, detecting the $PrP^{Sc}$-antibody complex and analysing the results of both probes. A monoclonal antibody termed 15B3 is used to detect $PrP^{Sc}$ in a $PrP^{Sc}$-antibody complex without prior protease-digestion of the tissue specimen to be examined. Biological material can be insoluble or soluble, and of any part of the body, e. g. from the brain in which case it is used in form of a homogenate or tissue sections, or any body fluid, e. g. cerebrospinal fluid, urine, saliva or blood. In the case of body fluids, fluid-resident cells, e.g. white blood cells in the case of blood expressing PrP, can be purified and analyzed.

The detection of the $PrP^{Sc}$-antibody complex is carried out on a smart planar optical element. This smart planar optical element is covalently coated with the described monoclonal antibodies. Analyte solutions are then guided to the sensing area of the chip via an appropriate fluid system. Analyte binding of the surface is recorded by registration of effective refractive index changes.

The present immunological detection procedures allow the diagnosis of prion diseases. With the tools of the present invention, tissue sections, tissue homogenates or body fluids of prion-infected animals, such as BSE-diseased cattle or humans having the CJD, can be screened for the presence of the protease-resistant, disease-specific isoform of the prion protein in its native form, be it soluble or insoluble.

Instead of directly analysing the binding of prions to antibodies immobilized on the chip surface, a competition assay is described. A protein ligand for anti-PrP antibodies is immobilized on the chip surface. Tissue homogenates or body fluids are incubated with anti-PrP antibodies. The mixture is then reacted with the molecules on the chip surface. Residual free antibodies will then bind and elicit a signal. In the case of an animal or human with prion disease. Part or all of the antibody will already be bound to PrP in the sample, thereby preventing the binding of the antibody to the chip surface, effectively reducing the signal observed with a sample from a normal animal or human. Reduction of the signal is therefore indicative of prion disease.

Method for the Identification of Ligands, Especially Receptors with Miniature Biosensor Chips Recombinant PrP is bonded on the optical chip. Homogenates containing presumed ligands are guided through the fluid system onto the optical chip. Molecules binding to the immobilized recombinant PrP increase the effective refractive index. Non-specifically binding bioconstituents are first removed by washing with appropriate solvents. Specifically binding ligands are then removed from the surface by selected desorption procedures. Ligands present in the eluate are identified and characterized.

Method for Screening Chemical or Pharmaceutical Libraries for the Identification of Small Compound Molecules Useful for Therapy Recombinant PrP or highly purified PrP is bonded on the optical chip. Homogenates containing presumed ligands are guided through the fluid system onto the optical chip. Molecules binding to the immobilized recombinant PrP alter the effective refractive index. The change of the effective refractive index indicates molecule binding.

Method for an Integrated Chip Able to Detect Several Ligands in Parallel

Smart planar optical elements are produced as described. Ligands or particularly monoclonal antibodies recognizing given molecules are bonded as described on these chips on distinct pads. The analyte to be examined is guided onto the chip. A laser or several laser beams are directed to the pads and the system detects the change of the effective refractive index at these pads. This allows performance of highly sensitive quantitation of various molecule concentrations in a complex analyte solution.

Small Portable Analytical Instrument

The described compact biosensor unit is designed as a portable autonomic unit capable of detecting one type or several types of molecules in analyte solutions or body fluids. Arrays of individual sensing areas are bioengineered with different amounts of one type of biomolecules (intrinsic gradients) or the surfaces contain varying amounts of several components. The portable analytical instrument can be used for outdoor or on-site testing.

The following examples serve to illustrate particular embodiments of the invention but they should not be considered a limitation thereof. The immunological procedures are outlined for the diagnosis of BSE in cattle, however, these procedures can also be applied for prion diseases in humans or animals, such as sheep, hamsters or mice. Furthermore, the described procedure can be applied for other diseases of human and animals utilizing appropriate sensing biomolecules and ligands.

EXAMPLES

Example 1

Design Fabrication and Testing of Biosensor Chips

Detection of immunological interactions between recombinant bovine PrP and monoclonal anti-PrP antibodies is accomplished by combining optical waveguide detection and light-addressable photobonding. In view of the exceedingly small quantities of analytes in test samples ($10^5$ to $10^8$ molecules), biosensor technologies must meet the requirements of high sensitivity and low non-specific binding. Designed for routine analysis, the detection system preferably consists of few components, fast in response (measuring time in the order of minutes or shorter) and suitable for mass production. The availability of disposable sensor devices, combined with multiple sensing and referencing pads on a single device is advantageous for diagnostic analysis.

I. Optical Waveguide Design and Fabrication

To adapt the resolution and dynamic range of the sensor chip to the needs of diagnostic application, corresponding substrates are fabricated. The grating structures are written by an e-beam pattern generator on quartz plates covered with chromium and a thin resist layer. After development, the pattern is transferred into the chromium and then by etching into the underlying quartz substrate to produce a surface relief grating with a depth of 5 to 10 nm. The pattern relief is electroformed to a nickel shim from which replicas are fabricated by hot embossing into a 250 $\mu$m thick polycarbonate foil (Röhm Europlex PC 99510). These embossings are generally 50×50 mm$^2$ in size and contain several grating regions. The waveguide is then fabricated by depositing thin TiO$^2$ films (typically about 160 nm thick) on the prestructured substrates by a modified d.c.-magnetron sputtering process. After cutting, the chips are glued onto glass substrates for stability reasons.

New nonlinear chirps of the grating lines are also fabricated allowing (at low resolution) highly sensitive signal analysis. A first layout is designed for a dual pad sensor with one sensing and one reference pad. For the analysis of complex systems, more than two pads are preferable (multichannel and multicomponent analysis). Standard industrial processes, as e.g. compact disc (CD) injection moulding, are preferred chip fabrication modes.

II. Optimization of Antibody Photobonding in View of Effective Reduction of Non-specific Binding in Real Fluids (e.g. Brain Homogenates)

Figure 3:
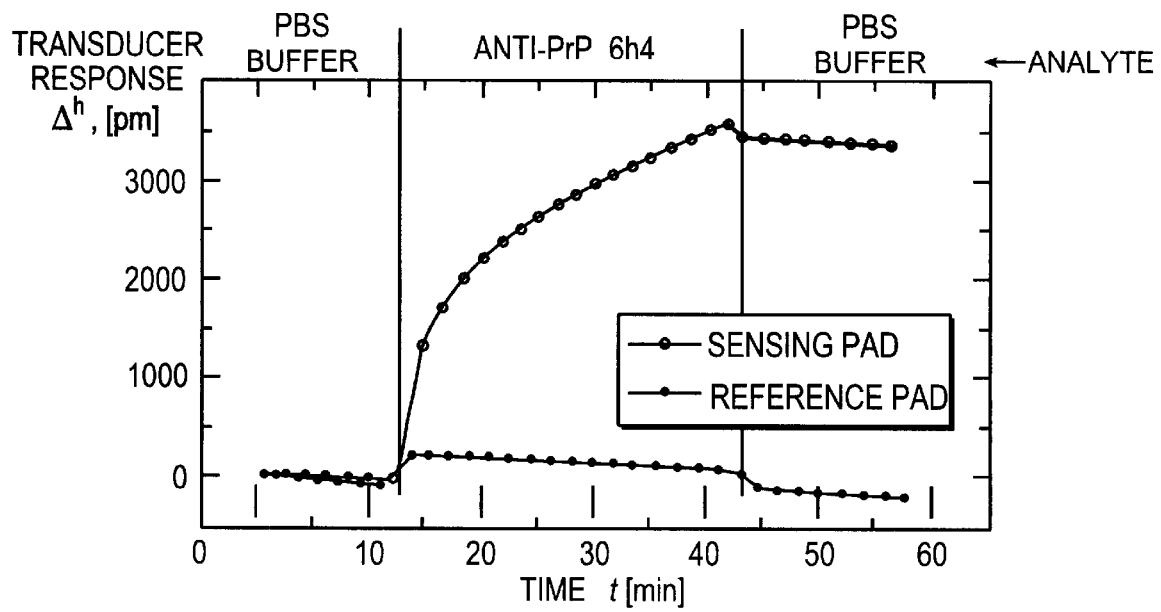
FIG. 3 is a diagram showing the successful binding of antibodies 6H4 to immobilized PrP. Recombinant bovine PrP was photoimmobilized on sensor chips. Incubation with PBS shows the baseline. After the addition of antibody 6H4 a change in adlayer thickness ($\Delta h_1$) is observed indicating binding of the antibody. A wash with PBS does not reduce the observed response.
Figure 4A:
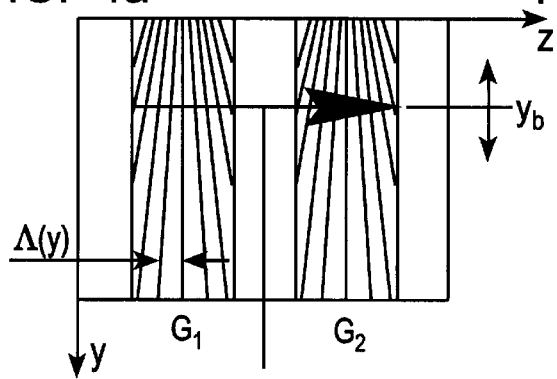
FIG. 4 shows in (a–c) a miniature sensor chip based on a dual pad chirped grating pad structure, in (d) a corresponding single chip sensor array, and in (e) a SPOT in a disc format.
Figure 4B:
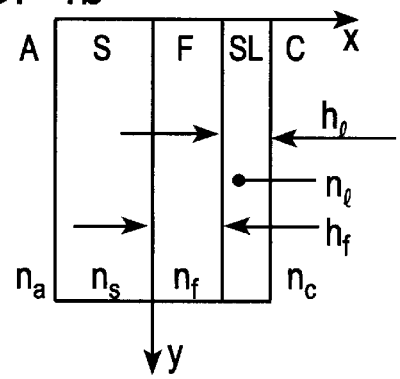
Figure 4C:
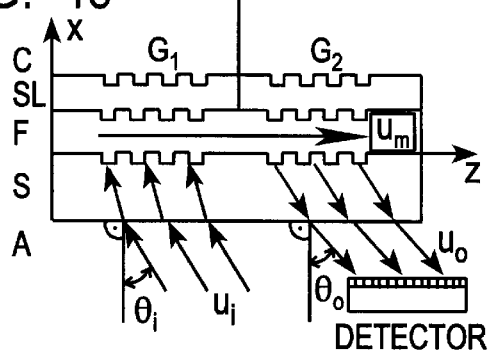
Figure 4D:
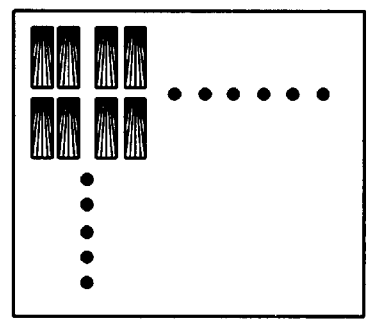
Figure 4E:
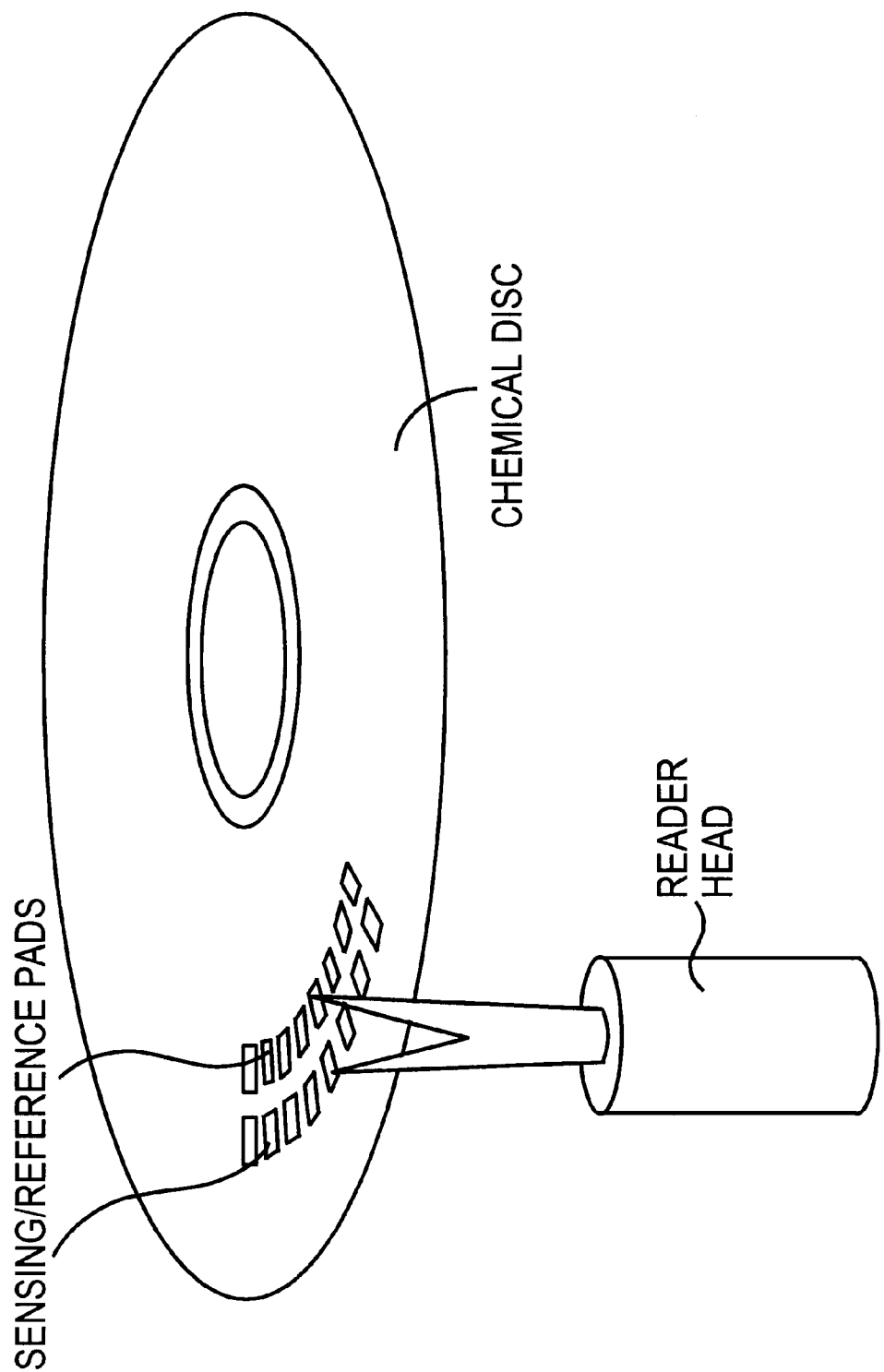

The experiment described in FIG. 3 was carried out by photobonding of PrP or anti-PrP antibodies to the chip surface by a method similar to the one described by (Gao, 1995). Alternatively, in order to maximize the density of antibody on the surface, maleimido-anyldiazinine mediated antibody immobilization procedures were applied. To achieve this, F(ab')$_2$ fragments are prepared. The disulphide bond in the constant region is selectively reduced and the free SH groups are used to immobilize the F(ab') fragments in a directed manner, i.e. the binding site pointing towards the liquid phase. This procedure ensures maximal packing of binding domains on the chip surface.

III. Optimization of Assay Parameters for the Detection of PrP in Brain Homogenates The antibody 6H4 recognizes also mouse PrP. This particular feature allows to control for the specificity of the system by using mouse brain homogenates from either wild type or PRP$^{0/0}$. Brain homogenates from either type are prepared under different conditions. The following buffers are used: 0.25 M sucrose, 20 mM HEPES; pH 7.0 or Sucrose/HEPES buffer containing in addition 2% N-lauryl sarcosine, 15 mM EDTA, 3 mM dithiotheitol. Sucrose/HEPES/EDTA buffer in combination with the following detergents were tested: Triton X-100, octyl glucoside and Tween 20 at various concentrations. In addition, DNAse was added into the homogenization buffer in order to reduce the viscosity due to DNA. These experiments showed the best calibration conditions that have to be used for an optimal signal to noise ratio. Along the same line recombinant PrP was reconstituted into PRP$^{0/0}$ mouse brain homogenates which allowed to directly compare the signal of a specific amount of PrP in its pure form and mixed into homogenates. Since proteinase K digested brain homogenates were used for the detection of PrP$^{BSE}$ recombinant PrP was also reconstituted into proteinase K-digested bovine brain homogenates which allowed to optimize the detection system for the actual conditions used for the detection of PrP$^{BSE}$.

Example 2

Building of a Biosensor Module

Since PrP$^{BSE}$ only occurs in combination with infectious particles, it is important to have a mobile biosensor module which can be used under biosafety conditions P2. A new compact and miniaturized IO sensor module was constructed and designed. A schematic drawing of such a module is shown in FIG. 5.

The complete module consists of three distinct submodules. The tasks of the submodules are illumination (i.e. to provide the optical input), signal transduction into an on-chip measuring variable and signal evaluation. In the sensor module shown in FIG. 5, the electrical input connector (laser driver) powers a laser diode (CD laser diode at 785 mm) for illumination of the sensor chip. A fluid handling system (tubings in the back) is used for analyte application. The sensor output signal is detected using an one-dimensional photodiode array. In this example, the electrical output signal is fed into a laptop computer (RS232 interface) via the connector to the right of the module.

Example 3

Detection of PrP$^{BSE}$

The functional biosensor module as described above was used to test the detection of bovine PrP$^{Sc}$. Specifically, the chips carrying either immobilized 6H4 or 15B3 were incubated with proteinase K-digested brain homogenates from normal or BSE-sick cattle. From Western blotting experiments, it is known that about 10–30% of total PrP in a BSE-infected brain correspond to PrP$^{BSE}$. Using the above described procedures, antibodies immobilized on the chips were incubated with proteinase K digested brain homogenates. No signal was observed in normal brain while specific binding was detected in homogenates from BSE-sick animals. For antibody 15B3, undigested homogenates were used and a signal was detected only in homogenates from BSE-sick cattle.

This method was further tested for the detection of PrP$^{BSE}$ in organs other than brain. The exquisite sensitivity of the biosensor system allowed to detect Pre SE in spinal fluid, lymphoid organs, blood, saliva or urine. Since the antibody 6H4 also recognizes mouse and sheep PrP, it was also used to test tissues from these animals. For sheep, it is known that placenta contains infectious material allowing to analyze the presence of PrP$^{Sc}$ in order to correlate infectivity and occurrence of PrP$^{Sc}$. In the mouse system, various tissues, such as spleen or intestine, are known to contain PrP$^{Sc}$ (Kitamoto, 1989). These experiments allowed to detect the amount of PrP$^{BSE}$ in various tissues and therefore allow also to estimate indirectly whether they may contain infectious substances.

Figure 2A:
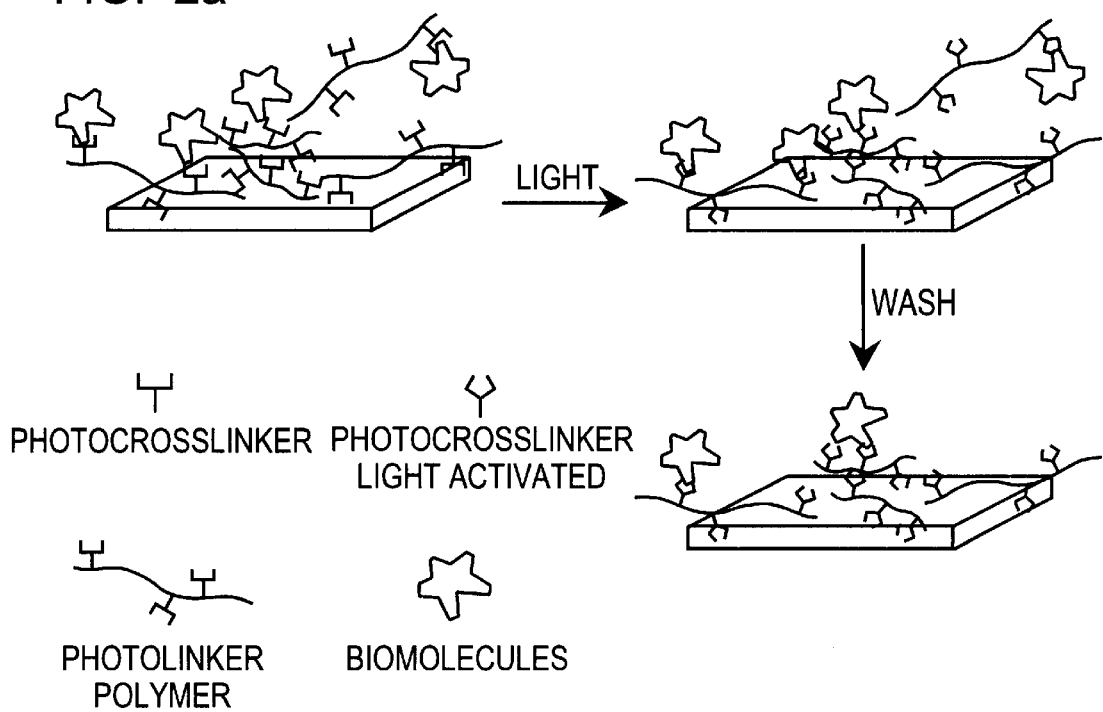
FIGS. 2a–2b show in (2a) the photolinker polymer mediated immobilization of biomolecules, where the photolinker consists of modified bovine serum albumin (TBSA), and in (2b), a preferred immobilization procedure suppressing non-specific bonding.
Figure 2B:
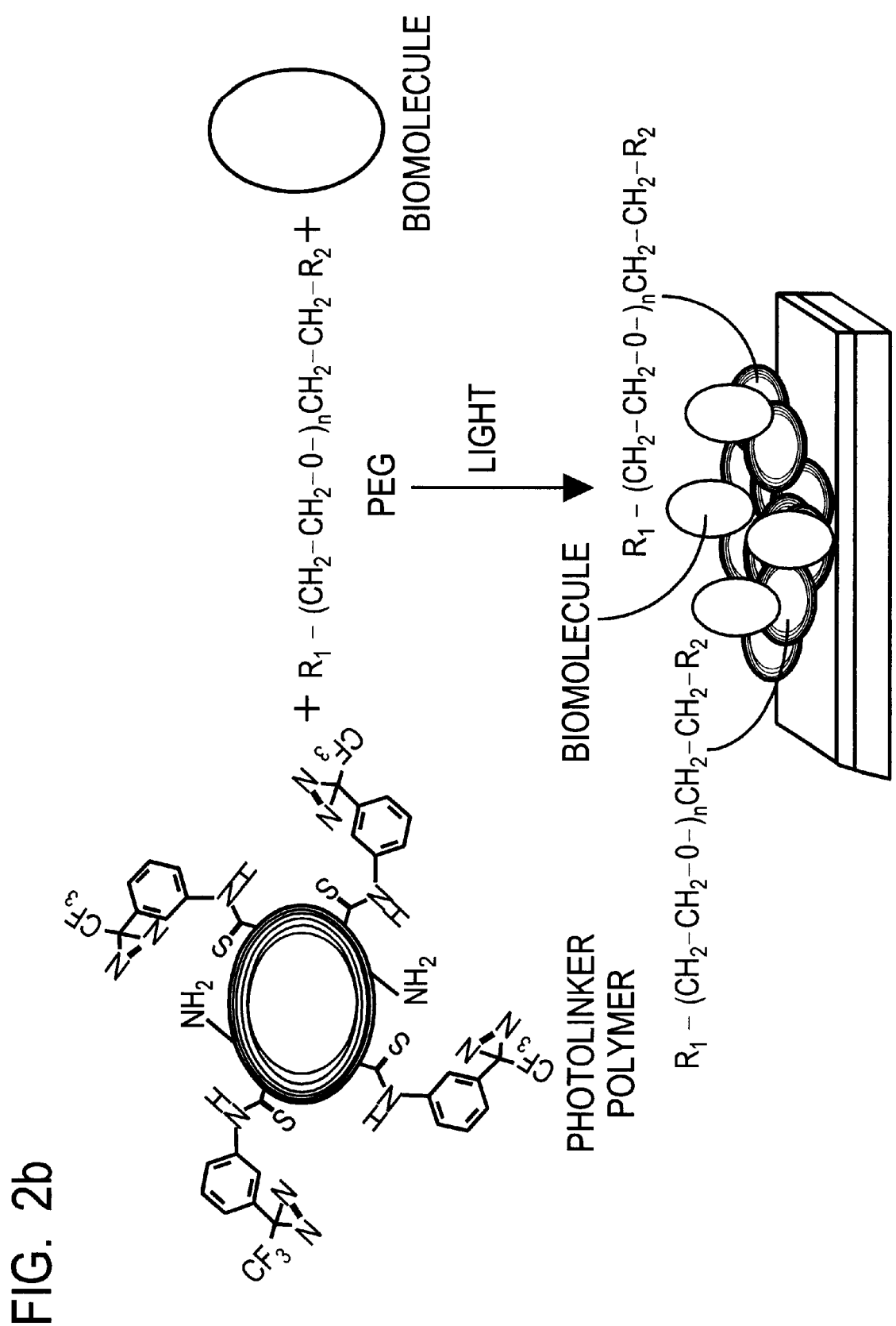

The following description details the preferred procedure to achieve suppression of non-specific binding (FIG. 2.b). The signal generated by specific interaction of the ligand binding molecule (e.g. anti-prion antibody) with the analyte PrP in real fluids can be as small as 8 to 20% of the signal produced by constituents of the real fluid. These latter constituents interact non-specifically with the engineered or pristine surface and thus, generates a sensor response. Suppression of such non-specific binding is achieved by including molecular components in the mixture used for surface engineering. Molecules added to the mixture used for surface bioengineering and photobonding include polyethylene glycol (PEG), amino-PEG, carboxy-PEG, polycarbohydrates (dextran, inulin), phospho-rylcholine containing polymers, selected components of the real fluid and mixtures thereof, fractions of complete control serum or homogenate not containing the analyte. In general terms, any molecular species effective in the suppression of non-specific binding is mixed with the analyte-binding molecule and the photo-linker polymer. Then the mixture is spread on the transducer surface and photobonded. For the detection of recombinant PrP in a non real fluid, the preferred components used for surface engineering include T-BSA (65% w/w), PEG (10% w/w) and monoclonal anti-PrP (25% w/w). For the detection of PrP in mouse brain homogenate, the preferred composition includes monoclonal anti-PrP 15B3 (12% w/w), T-BSA (58% w/w), PEG (12% w/w), carboxy PEG (8% w/w) and mouse brain homogenate (10% w/w added as solution). The brain homogenate included for surface engineering is taken from transgenic 0/0 mice, which do not produce PrP, neither cellular nor infectious forms. For each analyte the composition of the mixture used for surface engineering needs optimisation with respect to amount and type of constituents.

Example 4

Detection and Purification of a PrP Receptor

The biosensor system offers the invaluable advantage to visualize interactions of an immobilized protein (which would be PrP) with a ligand under nondenaturing conditions. This is exemplified by the interaction of PrP with the mAB 6H4 (see above FIG. 3). As described in the introduction, several intracellular ligands have been characterized, however, their role in the normal function of PrP or in disease is not clear. From the cell surface location of PrP as well as other indirect evidence it is supposed that a PrP receptor should exist. Recombinant mouse PrP immobilized on a biosensor chip was incubated with membrane fractions from mouse brain. Membranes were prepared on a sucrose gradient as described (Oesch, 1994). In those experiments a 120 kDa PrP ligand was detected in membrane fractions. In order to analyze the specificity of interaction, it was blocked by the addition of monoclonal antibodies. Both mAB 6H4 and 34C9 recognize the region proposed to be involved in an interaction between PrP molecules. Membranes from PRP$^{0/0}$ mice served as control, as it was known that the interaction of a membrane fraction with immobilized PrP was indeed due to PrP$^c$ (also found in membranes).

What is claimed is:

1. An optical sensor unit for the specific detection, identification or accumulation of chemicals or biomolocules in an analyt, said sensor unit comprising an integrated optical light pointer consisting of a laser light source, an optical detection module, and an integrated optical transducer chip whereon at least a layer of sensing biomolecules is covalently immobilized on a surface of a waveguiding layer by photopolymer mediated photochemical immobilization, the surface of the integrated optical transducer chip being grafted with lipids, forming lipid bilayer surfaces, whereby biospecific molecular interactions are identified by registration of changes in the effective refractive index, *aid optical detection module detecting readings from said intograted optical transducer chip initiated by striking said chip with laser light from said integrated optical light pointer.

2. An optical sensor unit according to claim 1, further comprising a fluid handling system and a computer.

3. An optical sensor unit according to claim 1, in which the transducer chip is of disposable nature.

4. An optical sensor unit according to claim 1, in which the optical transducer chip is made of a glass or organic polymer substrate, is coated with at least one hard dielectric layer to form a waveguide and is covered with a layer of sensing biomolecules.

5. An optical sensor unit according to claim 4, in which the organic polymer substrate is a polycarbonate.

6. An optical sensor unit according to claim 4, in which the hard dielectric layer is selected from the group consisting of silicon nitride, titanium dioxide, mixtures of silicon dioxide and titanium dioxide, $ZrO_2$, $HfO_2$, $Nb_2O_5$ and $Ta_2O_5$.

7. An optical sensor unit according to claim 6, in which the layer of sensing biomolecules is immobilized on individual areas by laser addressed covalent binding.

8. An optical sensor unit according to claim 7, in which the sensing biomolecules immobilized on individual sensing areas are different from each other.

9. An optical sensor unit according to claim 4, in which the immobilized sensing biomolecules are monoclonal or polyclonal antibodies, proteins or peptides thereof, agglutinins, lectins, polycarbohydrates, receptor proteins, low molecular weight haptens, nucleic acids.

10. An optical sensor unit according to claim 1, in which the layer of sensing biomolecules is immobilized in a patterned fashion on individual areas by mask-assisted, mask-free patterning or microstamping or microprinting procedures resulting in biosensor arrays.

11. An optical sensor unit according to claim 1 in which sensing areas on the integrated optical transducer chip are arranged in vertical and horizontal rows.

12. An optical sensor unit according to claim 1, in which the integrated optical transducer chip is a disc and the sensing areas are aligned in one or several concentric circles or in a spiral arrangement.

13. An optical sensor unit according to claim 1, in which the sensing biomolecules are immobilized individually or as mixtures on distinct sensor areas to establish gradient patterns.

14. An optical sensor unit according to claim 1, in which the sensing biomolecules are antibodies which recognize prions.

15. An optical sensor unit according to claim 1, in which 9 integrated optical transducer surface contains recombinant, normal or disease-specific prion proteins.

* * * * *